(12) United States Patent
Adney et al.

(10) Patent No.: US 7,449,550 B2
(45) Date of Patent: Nov. 11, 2008

(54) **SUPERACTIVE CELLULASE FORMULATION USING CELLOBIOHYDROLASE-1 FROM *PENICILLIUM FUNICULOSUM***

(75) Inventors: William S. Adney, Golden, CO (US); John O. Baker, Golden, CO (US); Stephen R. Decker, Berthoud, CO (US); Yat-Chen Chou, Golden, CO (US); Michael E. Himmel, Littleton, CO (US); Shi-You Ding, Golden, CO (US)

(73) Assignee: Alliance For Sustainable Energy, LLC, Golden, CO (US)

( * ) Notice: Subject to any disclaimer, the term of this patent is extended or adjusted under 35 U.S.C. 154(b) by 268 days.

(21) Appl. No.: 10/557,589

(22) PCT Filed: Feb. 27, 2003

(86) PCT No.: PCT/US03/06172
§ 371 (c)(1),
(2), (4) Date: Nov. 17, 2005

(87) PCT Pub. No.: WO2004/078919
PCT Pub. Date: Sep. 16, 2004

(65) Prior Publication Data
US 2007/0148730 A1 Jun. 28, 2007

(51) Int. Cl.
*C07K 14/00* (2006.01)
(52) U.S. Cl. .................................................. 530/350
(58) Field of Classification Search .................. None
See application file for complete search history.

(56) References Cited

U.S. PATENT DOCUMENTS

| 5,536,655 | A | 7/1996 | Thomas et al. |
| 2002/0061560 | A1 | 5/2002 | Lawlis |
| 2002/0155536 | A1 | 10/2002 | Van Den Brink et al. |

OTHER PUBLICATIONS

Munoz et al. Family 7 cellobiohydrolases from *Phanerochaete chrysosporium*: crystal structure of the catalytic module of Cel7D (CBH58) at 1.32 Å resolution and homology models of the isozymes, J Mol Biol. Dec. 14, 2001; Vo. 314 No. 5, pp. 1097-1111.*
Ward, M. et al., WO/1992/006209, "Trichoderma Reesei Containing Deleted Cellulase and Other Enzyme Genes and Cellulase Combination Therefrom" Apr. 16, 1992. Abstract.
Brooks et al., Proc. Annu. Fuels Biomass Symp. 2nd.
Ghose et al., Biotechnol. Bioeng., (1984), 26 (4): pp. 377-381 (1984).
Spindler et al., Biotechnology Letters, 14:403-407 (1992).
Baker et al., Hydrolysis of Cellulose Using Ternary Mixtures of Purified Cellulases, Appl. Biochem. Biotechnol. 70/72, pp. 395-403 (1998).
Baker et al., "A Membrane-Reactor Saccharification Assay to Evaluate the Performance of Cellulases Under Simulated SSF Conditions," Appl. Biochem. Biotechnol., 63/65 pp. 585-595 (1997).
Wu et al. Prog. Nucl. Acid. Res. Molec. Biol. 21:101-141 (1978).
Bhat, K. M. et al., "Characterization of the Major Endo-1,4-Beta-D-Glucanases from the Cellulase of Penicillium pinophilum/funiculosum" Biochem. Soc. Trans. 1989, vol. 17, No. 1, pp. 103-104.
Parr, S. R., "The Characterization of a Commercial Cellulase Product from Penicilium funiculosum by Fast Protein Liquid Chromatography," 1985, vol. 13, No. 2, pp. 452-453.
Wood, T.M., et al., "The Isolation, Purification and Properties of the Cellobiohydrolase Component of Penicillium funiculosum Cellulase," Biochem J. 1980, vol. 189, No. 1, pp. 51-65.

* cited by examiner

*Primary Examiner*—Robert B. Mondesi
(74) *Attorney, Agent, or Firm*—Paul J. White; John C. Stolpa; Mark D. Trenner

(57) ABSTRACT

Purified cellobiohydrolase I (glycosyl hydrolase family 7 (Cel7A) enzymes from *Penicillium funiculosum* demonstrate a high level of specific performance in comparison to other Cel7 family member enzymes when formulated with purified E1cd endoglucanase from *A. cellulolyticus* and tested on pretreated corn stover. This result is true of the purified native enzyme, as well as recombinantly expressed enzyme, for example, that enzyme expressed in a non-native *Aspergillus* host. In a specific example, the specific performance of the formulation using purified recombinant Cel7A from *Penicillium funiculosum* expressed in *A. awamori* is increased by more than 200% when compared to a formulation using purified Cel7A from *Trichoderma reesei*.

14 Claims, 5 Drawing Sheets

| SEQ ID NO: 7 | Nucleic acid sequence of P. funiculosum native cellobiohydrolase I | CAGCAAATTGGTACTTATACCGCTGAAACCCATCCCTCTCTGAGCTGGTCTACTTGCAAATCGGGT<br>GGTAGCTGCACCACAAACTCCGGTGCCATTACGTTAGATGCCAACTGGCGTTGGGTCCATGGTGT<br>CAATACCAGCACCAACTGCTACACTGGCAACACTTGGAATAGCGCCATCTGCGACACTGATGCAT<br>CCTGTGCCCAGGACTGTGCTCTCGATGGTGCTGACTACTCTGGCACGTACGGTATCACTACCTCCG<br>GCAACTCATTGCGCCTGAACTTCGTTACCGGTTCCAACGTCGGATCTCGTACTTACCTGATGGCCG<br>ATAACACCCACTACCAAATCTTCGATCTGTTGAACCAGGAGTTCACCTTCACCGTCGATGTCTCCC<br>ACCTCCCTTGCGGTTTGAACGGTGCCCTCTACTTCGTGACCATGGATGCCGACGGTGGCGTCTCCA<br>AGTACCCCAACAACAAGGCCGGTGCTCAGTACGGTGTTGGATACTGTGACTCTCAATGCCCTCGT<br>GACTTGAAGTTCATCGCTGGTCAGGCCAACGTTGAGGGCTGGACGCCCTCCGCCAACAACGCCAA<br>CACTGGAATTGGCAATCACGGAGCTTGCTGCGCGGAGCTTGATATCTGGGAGGCAAACAGCATCT<br>CAGAGGCCTTGACTCCTCACCCTTGCGATACACCCGGTCTATCTGTTTGCACTACTGATGCCTGCG<br>GTGGTACCTACAGCTCTGATCGTTACGCCGGTACCTGCGACCCTGATGGATGTGACTTCAACCCTT<br>ACCGCCTTGGTGTCACTGACTTCTACGGCTCCGGCAAGACCGTTGACACCACCAAGCCCTTTACCG<br>TTGTGACTCAATTCCTCACTAACGACGGTACCTCCACCGGTTCCCTCTCCGAGATCAGACGTTACT<br>ACGTTCAGAACGGCGTTGTCATCCCCCAGCCTTCCTCCAAGATCTCCGGAATCAGCGGAAATGTC<br>ATCAACTCCGACTACTGCGCTGCTGAAATTTCCACCTTTGGCGGGACTGCCTCCTTCAGCAAACAC<br>GGTGGCTTGACAAACATGGCCGCTGGTATGGAAGCTGGTATGGTCTTGGTCATGAGTTTGTGGGA<br>CGACTACGCCGTCAACATGCTCTGGCTCGACAGCACCTACCCTACAAACGCGACTGGTACCCCCG<br>GTGCCGCTCGTGGTACCTGCGCTACCACTTCTGGGGACCCCAAGACCGTTGAATCACAATCCGGC<br>AGCTCCTATGTCACCTTCTCTGACATTCGGGTTGGTCCTTTTCAATTCTACGTTCAGCGGTGGTTCTA<br>GCACCGGTGGCAGCACTACTACTACCGCCAGCCGCACCACCACCACCTCGGCCTCTTCCACCTCTA<br>CTTCCAGCACCTCTACTGGCACTGGAGTCGCTGGTCACTGGGGTCAGTGTGGTGGCCAGGGCTGG<br>ACTGGCCCTACCACCTGTGTTAGTGGAACCACATGCACCGTCGTGAACCCTTACTACTCTCAATGT<br>TTGTAG |
| SEQ ID NO: 8 | Amino acid sequence of expressed mature native P. funiculosum cellobiohydrolase | Gln Gln Ile Gly Thr Tyr Thr Ala Glu Thr His Pro Ser Leu Ser<br>Trp Ser Thr Cys Lys Ser Gly Gly Ser Cys Thr Thr Asn Ser Gly<br>Ala Ile Thr Leu Asp Ala Asn Trp Arg Trp Val His Gly Val Asn<br>Thr Ser Thr Asn Cys Tyr Thr Gly Asn Thr Trp Asn Ser Ala Ile<br>Cys Asp Thr Asp Ala Ser Cys Ala Gln Asp Cys Ala Leu Asp Gly<br>Ala Asp Tyr Ser Gly Thr Tyr Gly Ile Thr Thr Ser Gly Asn Ser<br>Leu Arg Leu Asn Phe Val Thr Gly Ser Asn Val Gly Ser Arg Thr<br>Tyr Leu Met Ala Asp Asn Thr His Tyr Gln Ile Phe Asp Leu Leu<br>Asn Gln Glu Phe Thr Phe Thr Val Asp Val Ser His Leu Pro Cys<br>Gly Leu Asn Gly Ala Leu Tyr Phe Val Thr Met Asp Ala Asp Gly<br>Gly Val Ser Lys Tyr Pro Asn Asn Lys Ala Gly Ala Gln Tyr Gly<br>Val Gly Tyr Cys Asp Ser Gln Cys Pro Arg Asp Leu Lys Phe Ile<br>Ala Gly Gln Ala Asn Val Glu Gly Trp Thr Pro Ser Ala Asn Asn<br>Ala Asn Thr Gly Ile Gly Asn His Gly Ala Cys Cys Ala Glu Leu<br>Asp Ile Trp Glu Ala Asn Ser Ile Ser Glu Ala Leu Thr Pro His<br>Pro Cys Asp Thr Pro Gly Leu Ser Val Cys Thr Thr Asp Ala Cys<br>Gly Gly Thr Tyr Ser Ser Asp Arg Tyr Ala Gly Thr Cys Asp Pro<br>Asp Gly Cys Asp Phe Asn Pro Tyr Arg Leu Gly Val Thr Asp Phe<br>Tyr Gly Ser Gly Lys Thr Val Asp Thr Thr Lys Pro Phe Thr Val<br>Val Thr Gln Phe Val Thr Asn Asp Gly Thr Ser Thr Gly Ser Leu<br>Ser Glu Ile Arg Arg Tyr Tyr Val Gln Asn Gly Val Val Ile Pro<br>Gln Pro Ser Ser Lys Ile Ser Gly Ile Ser Gly Asn Val Ile Asn<br>Ser Asp Tyr Cys Ala Ala Glu Ile Ser Thr Phe Gly Gly Thr Ala<br>Ser Phe Ser Lys His Gly Gly Leu Thr Asn Met Ala Ala Gly Met<br>Glu Ala Gly Met Val Leu Val Met Ser Leu Trp Asp Asp Tyr Ala<br>Val Asn Met Leu Trp Leu Asp Ser Thr Tyr Pro Thr Asn Ala Thr<br>Gly Thr Pro Gly Ala Ala Arg Gly Thr Cys Ala Thr Thr Ser Gly<br>Asp Pro Lys Thr Val Glu Ser Gln Ser Gly Ser Ser Tyr Val Thr<br>Phe Ser Asp Ile Arg Val Gly Pro Phe Asn Ser Thr Phe Ser Gly<br>Gly Ser Ser Thr Gly Gly Ser Thr Thr Thr Ala Ser Arg Thr<br>Thr Thr Thr Ser Ala Ser Ser Thr Ser Thr Ser Ser Thr Ser Thr<br>Gly Thr Gly Val Ala Gly His Trp Gly Gln Cys Gly Gly Gln Gly<br>Trp Thr Gly Pro Thr Cys Val Ser Gly Thr Thr Cys Thr Val<br>Val Asn Pro Tyr Tyr Ser Gln Cys Leu |
| SEQ ID NO: 9 | Nucleic acid sequence of P. funiculosum native signal sequence | ATGTCTGCCTTGAACTCTTTCAATATGTACAAGAGCGCCCTCATCTTGGGCTCCTTGCTGGCAACA<br>GCTGGTGCT |

FIG. 2

SUPERACTIVE CELLULASE FORMULATION USING CELLOBIOHYDROLASE-1 FROM *PENICILLIUM FUNICULOSUM*

CONTRACTUAL ORIGIN OF THE INVENTION

The United States Government has rights in this invention under Contract No. DE-AC36-99GO-10337 between the United States Department of Energy and the National Renewable Energy Laboratory, a division of Midwest Research Institute.

TECHNICAL FIELD

The invention pertains to the field of cellulases and, particularly, members of the glycosyl hydrolase Cel7 family, which is also known as the cellobiohydrolase I (CBH I) family of enzymes. More particularly, novel formulations using either purified native *P. funiculosum* Cel7A or purified recombinant *P. funiculosum* Cel7A (rCel7A) expressed from a transgenic *Aspergillus* host exhibit superior performance on pretreated corn stover compared with that formulation using purified *Trichoderma reesei* Cel7A.

BACKGROUND ART

Cellulosic biomass is a favorable feedstock for fuel ethanol production because it is both readily available and less expensive than either corn or sugarcane. Nevertheless, substantial problems must be overcome before a typical cellulosic feedstock can be utilized effectively and economically as a substrate for the fermentative production of ethanol. By way of example, cellulosic biomass feedstocks may include wood pulp or agricultural residues, such as corn stover, straw, grass, or weeds. A typical feedstock is comprised of approximately 35-45% cellulose, 30-40% hemicellulose, 15% lignin and 10% of other components. The cellulose fraction is composed of linear (and to a substantial extent, microcrystalline) polymers of the hexose sugar, glucose. Saccharification of cellulose releases sugars, which may be converted into ethanol or other products by fermentation. The hemicellulose fraction is comprised mostly of pentose sugars, including xylose and arabinose.

Alcohol products derived from cellulosic biomass are relatively expensive when compared to analogous fuels from other sources. A significant cost factor is the need to provide hydrolyzing enzymes, such as cellulases, that attack the cellulosic and/or hemicellulosic substrates to release sugars. These enzymes are produced by microorganisms, and may be purified from fermentation broth. The cost of cellulase is presently a significant component of the overall cost of biomass-derived ethanol. In the United States, ethanol production is heavily subsidized by tax incentives that encourage the use of ethanol in reformulated gasoline.

A variety of cellulases are known. Table 1 below lists various cellulases of the Cel7 family. Cel7 enzymes are the principal component in commercial cellulase formulations—typically accounting for most of the actual bond cleavage in the saccharification of cellulose. Cel7 cellobiohydrolases are members of the Class of beta proteins, the Superfamily of concanavalin A-like lectins/glucanases, and the Family of glycosyl hydrolase family 7 catalytic core proteins. The Cel7 family of enzymes may differ from one another by various insertions, deletions, and alterations in the catalytic domain and linker peptide. The cellulose binding domain of Cel7 enzymes is highly conserved. Cel7A from *Trichoderma reesei* is the most widely used CBH I commercial enzyme because it is capable of withstanding commercial process conditions and demonstrates the highest known level of saccharification in the entire family.

TABLE 1

VARIOUS CELLULOSE 1,4-β-CELLOBIOSIDASE MEMBERS

| Enzyme | Organism | GenBank/GenPept Accessions | Swiss Prot |
|---|---|---|---|
| Cellobiohydrolase I | *Agaricus bisporus* | Z50094 CAA90422.1 | Q92400 |
| exoglucanase C1 | *Alternaria alternata* | AF176571 AAF05699.1 | |
| Cellobiohydrolase I | *Aspergillus aculeatus* | AB002821 BAA25183.1 | O59843 |
| Cellobiohydrolase (CbhA) | *Aspergillus nidulans* | AF420019 AAM54069.1 | |
| Cellobiohydrolase (CbhB) | *Aspergillus nidulans* | AF420020 AAM54070.1 | |
| Cellobiohydrolase A (CbhA) | *Aspergillus niger* | AF156268 AAF04491.1 | |
| Cellobiohydrolase B (CbhB) | *Aspergillus niger* | AF156269 AAF04492.1 | Q9UVS8 |
| Cellobiohydrolase I | *Claviceps purpurea* | Y07550 CAA68840.1 | O00082 |
| Cellobiohydrolase I | *Cochliobolus carbonum* | U25129 AAC49089.1 | Q00328 |
| Cellobiohydrolase I | *Cryphonectria parasitica* | L43048 AAB00479.1 | Q00548 |
| Cellobiohydrolase I (Cel7A) | *Fusarium oxysporum* | L29379 AAA65587.1 | P46238 |
| Cellobiohydrolase 1.2 | *Humicola grisea* | U50594 AAD11942.1 AAN19007.1 | O94093 |
| Cellobiohydrolase I | *Humicola grisea* | D63515 BAA09785.1 X17258 CAA35159.1 | P15828 Q12621 |
| Cellobiohydrolase I | *Humicola grisea* var. *thermoidea* | AB003105 BAA74517.1 | O93780 |
| Cellobiohydrolase I.2 | *Humicola grisea* var. *thermoidea* | AF123441 AAD31545.1 | |
| Cellobiohydrolase I | *Melanocarpus albomyces* | | |
| Cellulose 1,4-β-cellobiosidase (Cel7B) | *Melanocarpus albomyces* | AJ515705 CAD56667.1 | |
| Cellobiohydrolase I | *Neurospora crassa* | X77778 CAA54815.1 | P38676 |
| Cellobiohydrolase | *Penicillium funiculosum* | AJ312295 CAC85737.1 | |
| Cellobiohydrolase I | *Penicillium janthinellum* | S56178 CAA41780.1 X59054 CAA41780.1 | Q06886 |
| Cellobiohydrolase | *Phanerochaete chrysosporium* | S40817 AAA09708.1 X54411 CAA38274.1 | Q01762 |

TABLE 1-continued

VARIOUS CELLULOSE 1,4-β-CELLOBIOSIDASE MEMBERS

| Enzyme | Organism | GenBank/GenPept Accessions | Swiss Prot |
|---|---|---|---|
| Cellobiohydrolase I-1 | *Phanerochaete chrysosporium* | M22220 AAB46373.1<br>Z22528 CAA80253.1 | P13860 |
| Cellobiohydrolase I-2 (Cel7D) | *Phanerochaete chrysosporium* | L22656 AAA19802.1<br>Z11726 CAA77789.1<br>Z11733 CAA77795.1<br>Z22527 CAA80252.1<br>Z29653 CAA82761.1<br>Z29653 CAA82762.1 | Q09431 |
| Cellobiohydrolase 1 (Cbh1A) | *Talaromyces emersonii* | AF439935 AAL33603.2<br>AY081766 AAL89553.1 | |
| Cellobiohydrolase I (Cel7A) | *Trichoderma reesei* (*Hypocrea jecorina*) | X69976 CAA49596.1 | P00725 |
| Cellobiohydrolase I | *Trichoderma viride* | X53931 CAA37878.1 | P19355 |
| Cellobiohydrolase I | *Trichoderma viride* | AB021656 BAA36215.1 | O93832 |
| Cellobiohydrolase I (CbhI) | *Volvariella volvacea* V14 | AF156693 AAD41096.1 | |

Cellulases often demonstrate enzymatic synergy in mixtures with other hydrolyzing enzymes; for example, between one enzyme that attacks cellulose and another that attacks hemicellulose. Various efforts have been made to provide transgenic organisms with one or more recombinant genes and obtain multiple functionality from a single organism, for example, as described in U.S. Pat. No. 5,536,655 issued to Thomas et al. for the gene encoding EI endoglucanase from *Acidothermus cellulolyticus*.

United States patent application publication US 2002/0155536 to Van en Brink et al. discloses a method of isolating DNA sequences coding for one or more proteins of interest advantageously using an *Aspergillus* host. More specifically, cDNA is prepared from an organism of interest. Fragments of the cDNA are inserted into a vector to obtain a cDNA library. Subsequent transformation of the cDNA library into filamentous fungi, such as *Aspergillus*, facilitates screening for clones that express proteins of interest.

The '536 patent publication describes an expression system using filamentous fungi, such as *Aspergillus*, to provide host cells to screen for proteins of interest. Expression in an *Aspergillus* host renders the cloned polypeptide sequences more easily detectable due to a higher secretory capacity and less glycosylation, as by way of example, in *Aspergillus nigeras* compared to yeast. The '536 patent does not teach that *P. funiculosum* Cel7A can be secreted from *Aspergillus awamori* with full functionality.

United States patent application publication US 2002/0061560 to Lawlis describes a method of obtaining a secretory protein at a higher level in filamentous fungi, for example, *Aspergillus awamori*. More specifically, the coding sequence for the protein of interest is fused with DNA fragments encoding signal peptide, a cleavable linker peptide, and a portion of a protein native to the filamentous fungal host (i.e., protein that is normally secreted from *Aspergillus*). The '560 publication pertains to increased quantities of secreted proteins, and does not teach that *P. funiculosum* Cel7A can be secreted with full functionality.

WO 92/06209 to Ward et al. relates to an improved process for transforming the filamentous fungus *T. reesei*. *T. reesei* cells are treated with homologous DNA originally derived from *T. reesei*. The homologous DNA is provided with a selectable marker, which is used to select transformants. Although CBH I is used as an example, nothing related specifically to the processing and secretion of *P. funiculosum* Cel7A is taught or disclosed.

Efforts in recombinant technologies that pertain to the production of cellulases emphasize the production of cellulase in greater quantity or the production of cellulase having greater activity measured as conversion efficiency over time. It is notoriously difficult to compare the activity or performance of cellulases on naturally occurring cellulosic substrates. The naturally occurring substrates vary in composition, which makes it difficult to provide a uniform basis of comparison. Additionally, one is prone to draw unwarranted conclusions where higher concentrations of enzymes may produce surface effects when the enzyme interferes with itself. Similarly unwarranted conclusions may be drawn where adsorption effects (i.e., enzyme loss) impair the activity of lower cellulase concentrations. When it becomes necessary to measure performance with exactitude, commercial enterprises often choose to consult institutions, such as the National Renewable Energy Laboratory located in Golden, Colorado.

Transgenic expression of genes does not necessarily result in the production of useful cellulase. For example, glycosylation by yeast used to express the Cel7 family enzymes may render the enzymes less effective or ineffective. The choice of host organism is limited to those organisms that can survive commercial process conditions, for example, the Direct Microbial Conversion (DMC) process or the Simultaneous Saccharification and Fermentation (SSF) process. In the DMC method, a single microbial system both produces cellulase and ethanol as a fermentation product. The SSF method utilizes two biological elements, one that produces cellulase enzyme and the other, which ferments sugar to ethanol. The DMC process is described in (Brooks et. al., Proc. Annu. Fuels Biomass Symp., $2^{nd}$ (1978). The SSF process is described in Ghose et. al., Biotechnol. Bioeng., (1984), 26 (4): 377-381(1984)., e.g., as described by Spindler et al, Biotechnology Letters, 14:403-407 (1992). By way of example, SSF process conditions may impose a pH of 4.5 to 5.5 and a temperature from 30° C. to 38° C. It can be difficult to choose a suitable host capable of both expressing a useful form of the cellulase of interest and surviving the process conditions where the cellulase is also active under process conditions.

SUMMARY

The present invention advances the art and overcomes the problems outlined above by providing a cellobiohydrolase I family 7 (Cel7) enzyme formulation using the native Cel7A from *Penicillium funiculosum* or its recombinant analogue expressed in a transgenic filamentous fungi, e.g., *Aspergillus* sp. The Cel7A enzyme formulation demonstrates an unusually high (if not unprecedented) level of specific performance in saccharification of cellulose.

The Cel7 enzyme formulation contains Cel7A enzyme obtained from *P. funiculosum* or a recombinant analog thereof, for example, a polypeptide having a sequence of SEQ ID NO. 9. The Cel7A enzyme may be combined with an endoglucanase present in amount ranging from one percent (1%) to twenty percent (20%) of the molar concentration of the Cel7A enzyme.

The Cel7A enzyme may be a recombinantly expressed enzyme from a transgenic filamentous fungus. Examples of the transgenic filamentous fungus include *Aspergillus* sp., *Trichoderma* sp., and *Penicillium* sp. Further examples of the transgenic filamentous fungus include *Aspergillus awamori, Aspergillus niger, Trichoderma reesei*, and even *Penicillium funiculosum* expressing a transgene encoding the Cel7 enzyme under control of a promoter that is non-native to *Penicillium funiculosum*.

The cellobiohydrolase formulation exhibits specific performance in saccharification of biomass cellulose that exceeds by at least two-fold (i.e., 200%) the specific performance of a comparable cellobiohydrolase formulation where Cel7A cellulase from *Trichoderma reesei* is substituted for the Cel7A enzyme. This level of specific performance is heretofore unknown from Cel7 family enzymes. By way of example, the specific performance may be measured on pretreated corn stover.

The endoglucanase may be EI endoglucanase mixed with the Cel7 enzyme, for example, in a 95:5 molar ratio of the Cel7A enzyme to EI endoglucanase. Additional hydrolyzing enzymes, such as β-glucosidase, may be added to the mixture.

Recombinant expression of the Cel7 may be achieved by transforming a filamentous fungus with a gene from *Penicillium funiculosum*. The gene encodes a Cel7 enzyme that is foreign to the filamentous fungus and/or places the coding region under the control of a non-native promoter. The recombinant Cel7 (rCel7) is expressed by the filamentous fungus using biological processes that operate on the nucleic acid sequence to produce rCel7. The rCel7 enzyme may be purified, e.g., by chromatography, to a concentration that exceeds a concentration obtainable from natural expression processes.

A specific embodiment of the instrumentalities described herein should not be interpreted to define the invention in unduly narrow terms. This is because the specific embodiment teaches by way of example, and not by limitation. *Aspergillus awamori* is used as a host organism to express a particular form of rCel7A enzyme, namely, using a gene encoding Cel7A isolated from *Penicillium* and, more particularly, from *Penicillium funiculosum*.

The Cel7A enzyme represented by SEQ ID NO. 8, after expression by *A. awamori*, is characterized by a thermal denaturation temperature of 66.8° C., as measured by differential scanning microcalorimetry (DSC) at pH 5.0 and a scan rate of 60° C./hour.

Standards for measuring specific performance and other characteristics of cellulases are known in the art. For example, useful techniques of this type are taught by "Hydrolysis of Cellulose Using Ternary Mixtures of Purified Cellulases," J. O. Baker, C. I. Ehrman, W. S. Adney, S. R. Thomas, and M. E. Himmel, *Appl. Biochem. Biotechnol.*, 70/72, 395-403, (1998); and "A Membrane-Reactor Saccharification Assay to Evaluate the Performance of Cellulases Under Simulated SSF Conditions," J. O. Baker, T. B. Vinzant, C. I. Ehrman, W. S. Adney, and M. E. Himmel, *Appl. Biochem. Biotechnol.*, 63-65, 585-595, (1997).

Different substrates may be used in testing the Cel7 enzyme formulation. For example, pretreated wood pulp or pretreated agricultural residues may be used for comparative testing purposes to confirm the superior specific performance. Pretreated corn stover is often used as a basis of comparison. Efficient enzymatic hydrolysis of these substrates by cellulase often requires the synergistic cooperation of at least two types of enzymes, namely, endoglucanases and exoglucanases, such as cellobiohydrolase. According to these protocols, the specific performance may be measured using a mixture of enzymes, for example, a mixture of rCel7A (or native Cel7A) and endoglucanase at a molar ratio of 95:5.

Increased specific performance of Cel7A may be facilitated in reaction processes by the addition of other hydrolyzing enzymes, such as β-glucosidase. A particularly useful enzyme mixture includes *T. reesei* Cel7A mixed in a 95:5 molar ratio with *A. cellulolyticus* EIcd endoglucanase, such as EI endoglucanase expressed from the *Acidothermus cellulolyticus* gene reported in U.S. Pat. No. 5,536,655 issued to Thomas et al., which is incorporated by reference herein. Another useful additional enzyme is β-glucosidase from *Aspergillus niger*, as reported in "Hydrolysis of Cellulose Using Ternary Mixtures of Purified Cellulases," J. O. Baker, C. I. Ehrman, W. S. Adney, S. R. Thomas, and M. E. Himmel, *Appl. Biochem. Biotechnol.*, 70/72, 395-403, (1998). This formulation shows superior performance. Other hydrolyzing enzymes that may be included in such mixtures include members of Family Cel6.

The *P. funiculosum* rCel7A enzyme may be purified from cultures of native organisms or recombinant hosts. Purification may be accomplished by chromatography to levels of, for example, 50%, 75%, 90%, or research grade purity.

BRIEF DESCRIPTION OF THE DRAWINGS

FIG. 2 shows DNA and polypeptide sequences of interest for Cel7A enzyme isolated from *P. funiculosum*

DETAILED DESCRIPTION

There will now be shown and described a process for the production of rCel7 in *Aspergillus* and, specifically *P. funiculosum* rCel7A expressed in *A. awamori*. The presentation of a specific embodiment according to the various embodiments and instrumentalities described herein should not unduly limit the scope of the invention, because the teaching is by way of example.

Procedures for constructing recombinant molecules are disclosed by Sambrook et al., supra. Briefly, a DNA sequence encoding a Cel7A enzyme from *Penicillium funiculosum*, or its functional derivatives exhibiting Cel7 activity, may be recombined with vector DNA in accordance with conventional techniques. These techniques and materials include, for example, restriction enzyme digestion to provide appropriate termini, filling in of cohesive ends as appropriate, alkaline phosphatase treatment to avoid undesirable joining, and blunt-ended or cohesive-ended ligation with appropriate ligases. Part or all of the genes may be synthesized chemically in overlapping fragments which are hybridized in groups and ligated to form longer double-stranded DNA molecules. The resulting vector may then be introduced into a host cell by transformation, transfection, techniques such as electroporation, etc. Techniques for introducing a vector into a host cell are well known.

A vector is a DNA molecule, often derived from a plasmid, bacteriophage or hybrid, into which fragments of DNA may be inserted or cloned. A vector usually contains one or more unique restriction sites, and may be capable of autonomous replication or integration into the genome of a defined host organism such that the cloned sequence is reproducible.

Figure 1:
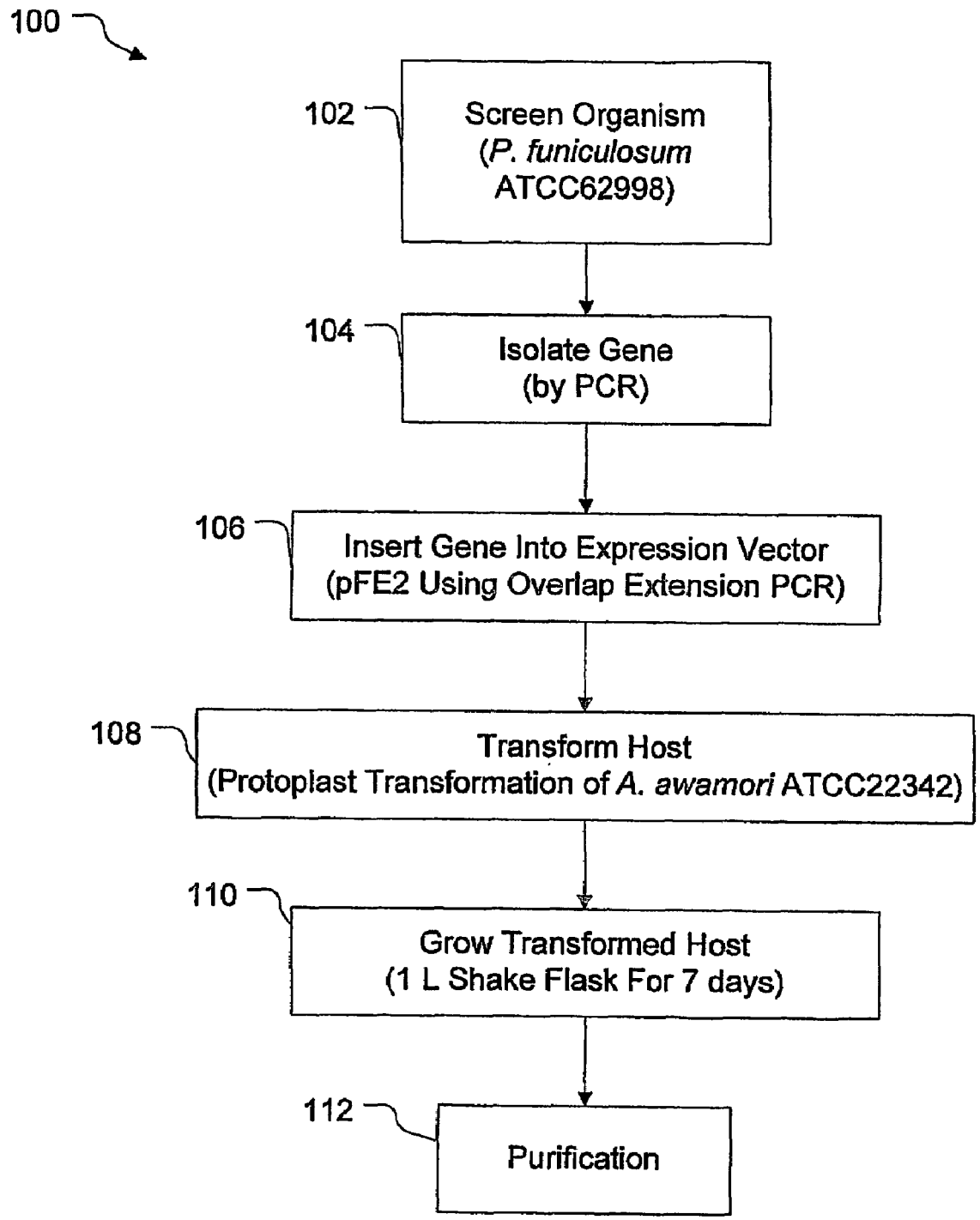
FIG. 1 is a schematic block diagram that shows a process for producing a recombinant Cel7A enzyme.

FIG. 1 is a process diagram 100 showing steps for the production of rCel7A from *P. funiculosum*. In step 102, a culture of a source organism, such as the source organisms identified above in Table 1, are screened for Cel7 activity. For example, *P. funiculosum* (ATCC62998) is screened to identify the presence of Cel7A. In step 104, primers are constructed based upon the presumed commonality of conserved sequences among the respective domains, such as the catalytic domain in the Cel7A family. The gene is then isolated by polymerase chain reaction (PCR). Step 106 entails inserting the gene into an expression vector, for example, using overlap extension PCR to insert the gene into expression vector pFE2. In step 108, the expression vector is used in host transformation, specifically protoplast transformation of *Aspergillus awamori* ATCC22342. A transformed strain that is confirmed to carry the rCel7A gene is grown for a period of time in step 110, and the rCel7A is purified in step 112.

The Cel7A family genes can be cloned for expression in *Aspergillus* and other filamentous fungi using recombinant DNA techniques, as will be described below and illustrated by specific example. Variations on laboratory techniques are well known and may be adapted to implement the instrumentalities described herein. In addition to the disclosed embodiments, the DNA cloning process can be facilitated through a variety of other means, such as application of recombinant DNA techniques, the polymerase chain reaction techniques (PCR) or DNA synthesis of the gene. Techniques for synthesizing oligonucleotides are disclosed by, for example, Wu et al, Prog. Nucl. Acid. Res. Molec. Biol. 21:101-141 (1978).

Standard reference works setting forth the general principles of recombinant DNA technology and cell biology include, for example, Watson et al., Molecular Biology of the Gene, Volumes I and II, Benjamin/Cummings Publishing Co., Inc., Menlo Park, Calif. (1987); Darnell et al., Molecular Cell Biology, Scientific American Books, Inc., New York, N.Y. (1986); Lewin, Genes II, John Wiley & Sons, New York, N.Y. (1985); Old et al., Principles of Gene Manipulation: An Introduction to Genetic Engineering, 2nd Ed., University of California Press, Berkeley, Calif. (1981); Sambrook et al, (Molecular Cloning: A Laboratory Manual, 2nd Edition, Cold Spring Harbor Press, Cold Spring Harbor, N.Y. (1989)) and Albers et al., Molecular Biology of the Cell, 2nd Ed., Garland Publishing, Inc., New York, N.Y. (1989).

The following nonlimiting examples establish preferred materials and methods for practicing the process steps of FIG. 1, as well as for use in comparing the specific activities of rCel7A enzymes

EXAMPLE 1

Isolating a Cel7A Gene from *P. funiculosum*

Figure 3:
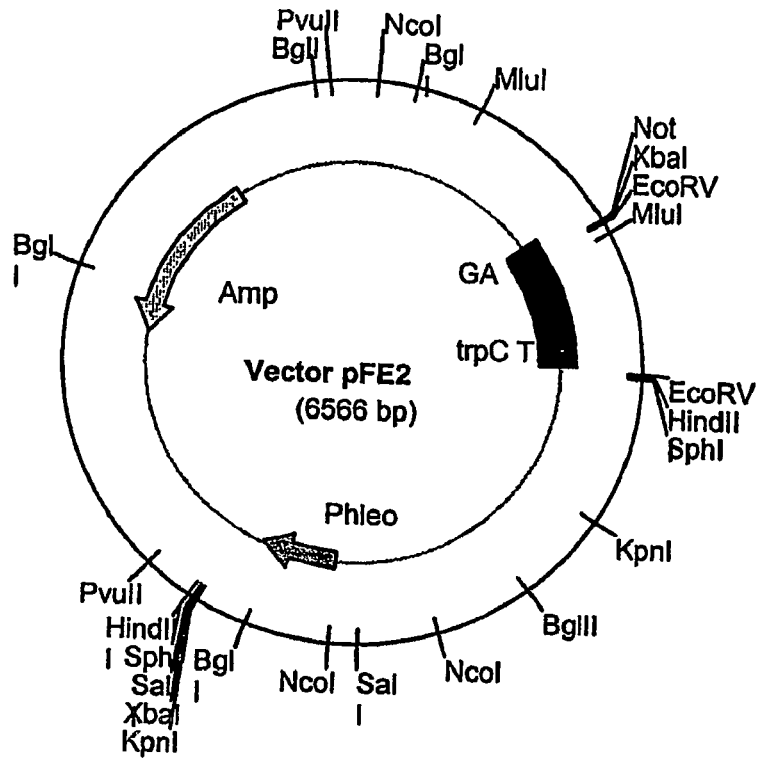
FIG. 3 depicts a vector that may be recombined with the Cel7'coding region and/or a promoter sequence for use in transforming the filamentous fungus according to the instrumentalities described herein.

The coding sequence for the cel7A gene from *P. funiculosum* (ATCC 62998) (SEQ ID NO. 7 of FIG. 2) was inserted and expressed in the fungal host *Aspergillus awamori* (ATCC 22342) using the fungal expression vector pEE2. As shown in FIG. 3, the pFE2 vector is an *E. coli—Aspergillus* shuttle vector, and contains elements required for maintenance in both hosts. The pFE2 vector directs the expression and secretion of the protein of interest as a fusion protein with a portion of the glucoamylase (GA) gene fused to the cel7A gene. The vector contains the *Streptoalloteichus hindustanus* phleomycin resistance gene (Phleo) under the control of the *A. niger* β-tubulin promoter, for positive selection of *Aspergillus transformants*. The vector also contains a β-lactamase gene for positive selection using ampicillin in *E. coli*, and the *A. niger* trpC terminator (trpC T). In this case, the rCel7 protein from *P. funiculosum* was expressed with its own secretion signal peptide by replacing the glucoamylase signal by PCR overlap extension and was expressed under the control of the *Aspergillus niger* GA promoter.

Figure 4:
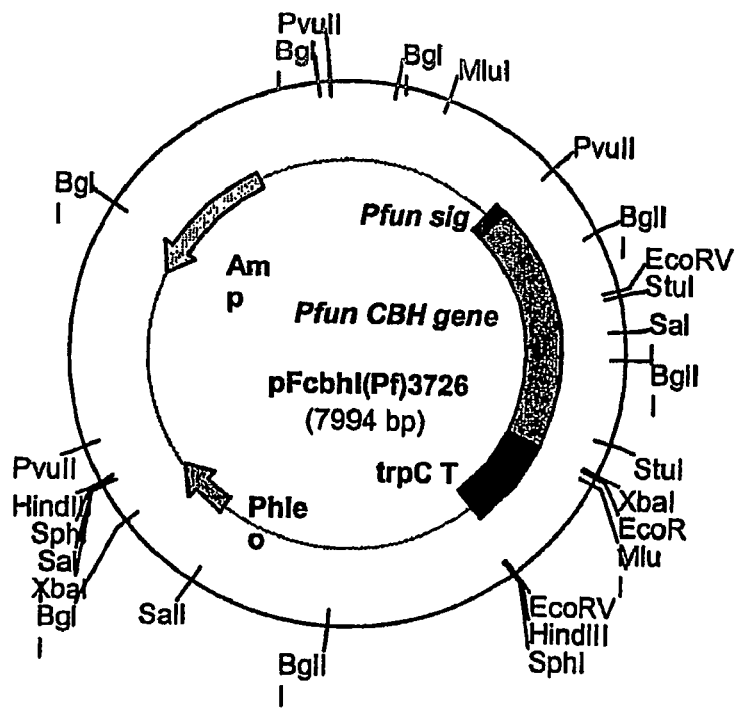
FIG. 4 depicts the vector of FIG. 3 after recombination.

As shown in FIG. 4, the construct used to produce recombinant Cel7 enzyme was designated pFEcbhI(Pf)3726 and was designed to contain the native *P. funiculosum* signal sequence (SEQ ID. NO. 8; Pf signal) with the native coding sequence (*P. fuliculosum* cbhI gene) for the structural protein. The 1.5-kb *P. funiculosum* cbhI structural gene (including the signal sequence starting with ATG codon and the mature protein coding sequence, which ends with TAG stop codon) was used to replace the GA signal sequence in the pFE2 vector. The GA signal sequence was replaced using overlap extension PCR where the native *P. funiculosum* structural gene was placed precisely under the GA promoter and regulatory region in pFE2. In addition, a NotI restriction site was added after the TAG codon (see primer PfcbhINotI(R)) to position the gene immediately before the trpC T terminator region in pFE2.

The regulatory region containing GA promoter and native *P. funiculosum* Cel7A signal region (0.9 kb) was PCR amplified using PfuI with the following oligonucleotide primers:

FE2-2(F): 5'GTATACACGCTGGATCCGAACTCC 3' (SEQ ID NO. 1)

FE2-PfcbhI(R):
5'GTTCAAGGCAGACATTGCTGAGGTG-TAATGATGC 3' (SEQ ID NO. 2)

[5'PfcbhI signal(tail)] [Sequence before GA signal]

The template used for the PCR was pFE2 vector. The bolded region of SEQ ID NO. 2 above anneals to the sequence immediately before the GA signal sequence in pFE2. The underlined region is complementary to the 5' *P. funiculosum* CBH I signal coding sequence. After this round of PCR, the regulatory region included the GA promoter region from pFE2 and 5'end of native *P. funiculosum* Cel7A signal sequence.

The structural gene of *P. funiculosum* Cel7A was amplified using the following primers:

PfcbhI-FE2(F):
5'GCATCATTACACCTCAGCAATGTCTGC-CTTGAAC 3' (SEQ ID NO. 3) [Sequence before GA signal (tail)] [5'Pf CBH I signal]

PfcbhINotI(R):
5'ATAAGAATGCGGCCGCCTACAAACAT-
TGAGAGTAGTAAGGG 3' (SEQ ID NO. 4).

Genomic DNA of *P. funiculosum* (ATCC 62998) was used as template for the PCR reaction. The bolded sequence in PfcbhI-FE2 (F) primer (SEQ ID NO. 3) annealed with pFE2 vector and not the *P. funiculosum* cel7A coding sequence. Following this round of PCR the 5'-end of the cel7A structural gene contained the extra sequence of the GA signal.

To combine the GA promoter and GA regulatory region from pFE2 and the *P. funiculosum* cel7 structural gene, a third round of PCR was conducted using the two PCR products described above and primers FE2-2 (F) (SEQ ID NO. 1) and PfcbhINotI(R) (SEQ ID NO. 4). The product (2.6 kb) was ligated in a T/A cloning vector, pGEMTeasy, which is obtainable on commercial order from Promega of Madison, Wis., and used to transform *E. coli* DH5α. Transformants with correct inserts were identified by colony PCR screening using a primer pair including:

Pf3 (F): ACTTCGTTACCGGCTCTAACG (SEQ ID NO. 5) and

Pf4(R): GAAGTCACATCCGTCAGGGTC (SEQ ID NO. 6).

The primer pair Pf3 (F) (SEQ ID NO. 5) and Pf4(R) (SEQ ID NO. 6) is internal to *P. funiculosum* Cel7A. Plasmid DNA was extracted from several of these correct transformants and digested with Ba followed by Klenow polymerase treatment to generate the blunt ends. BamHi is located in the 5'end of the 2.6-kb fragment and intrinsic to the GA promoter region of pFE2 vector. A 2.4-kb fragment was obtained by NotI digestion of the BamHI/Klenow linearized plasmid. NotI was included in the PfcbhINotI(R) for cloning purposes. To transfer this 2.4-kb fragment into pFE2, pFE2 was digested with SacI and blunt-ended with T4 DNA polymerase followed by digestion with NotI. A 5.5-kb vector fragment was recovered by gel extraction and ligated to the 2.4-kb fragment. The recombinant plasmid was named pFcbhI(Pf)3726.

After transformation in DH5α and confirmation of the plasmid by colony PCR and restriction digestion pattern, the plasmid was used to transform *A. awamori* by spheroplast transformation. Zeocin-resistant transformants were grown in liquid medium CMZ300 (CM+Zeocin 300 μg/ML) for 3-4 days and supernatant analyzed by activity on p-nitrophenol β-D lactopyranoside activity assay. One of the positive clones was grown in 1-L CMZ300 medium for 7-10 days and supernatant subjected to protein purification and analysis. Expression products of this clone were confirmed to contain the recombinant Cel7A enzyme isolated from *P. funiculosum* (SEQ ID NO. 8).

EXAMPLE 2

Transforming *A. awamori*

*Aspergillus awamori* (ATCC22342) spore stocks were stored at −70° C. in 20% glycerol, 10% lactose. After thawing, 200 μL of spores were inoculated into 50 mL CM-glucose broth (5 g·L$^{-1}$ Yeast Extract; 5 g·L$^{-1}$: Tryptone; 10 g·L$^{-1}$ Glucose; 20X Clutterbuck's Salts (120.0 g·L$^-$Na$_2$NO$_3$; 10.4 g·L$^{-1}$ KCl; 10.4 g·L$^{-1}$ MgSO$_4$.7H$_2$O; 30.4 g·L$^{-1}$ KH$_2$PO$_4$) 50 mL·L$^{-1}$) at pH 7.5 in each of eight-baffled 250 mL Erlenmeyer flask. The cultures were grown at 28° C., 225 rpm for 48 h.

The mycelial balls were removed by filtration through sterile Miracloth (Calbiochem, San Diego, Calif.) and washed thoroughly with sterile KCM (0.7M KCl, 10 mM MOPS, pH 5.8) to remove ungerminated spores. Approximately 10 g wet weight of washed mycelia were transferred to 50 mL KCM+ 250 mg Lysing Enzyme from *Trichoderma harzianum* (Sigma-Aldrich, St. Louis, Mo.) in a 250 mL baffled Erlenmeyer flask. The digestion mixture was incubated overnight at 30° C., 80 rpm.

Following digestion, the mycelia were titurated with a 25 mL disposable pipette to loosen the hyphal cells and filtered through sterile Miracloth into 50 mL conical centrifuge tubes. The spheroplasts were pelleted at 1500 x g for 12 min and resuspended in 0.7M KCl by gentle tituration with a 25 mL pipette. This was repeated once. After a third pelleting, the spheroplasts were resuspended in 10 mL KC (0.7M KCl; 50 mM CaCl$_2$), pelleted and resuspended in 1.0 mL KC using a wide-bore pipet tip.

The washed spheroplasts were transformed by adding 12.5 μL PCM (40% PEG 8000; 50 mM CaCl$_2$; 10 mM MOPS pH 5.8) and 5 μL DNA (~0.5 μg/μL) to 50 μL of spheroplasts in sterile 1.5 mL Eppendorf tubes. After incubation on ice for 45 minutes, 0.5 mL of room temperature PCM was added to the transformation mixture and was mixed by inversion and gentle vortexing. The mixture was incubated at room temperature for 45 minutes. One milliliter of KC was added and mixed. Selection of transformants was by zeocin resistance. The mixture was allocated between four tubes (10 mL each) of CM top agar at 55° C., which were each poured over a 15 mL CM plate with 170 μg/mL zeocin. The plates were incubated at 28° C. for 2-3 days. Subsurface colonies were partially picked with a sterile wide bore pipet tip, exposing the remaining part of the colony to air and promoting rapid sporulation. After sporulation, spores were streaked onto several successive CM plates with either 100 or 300 μg/mL zeocin added. After a monoculture was established, heavily sporulated plates were flooded with sterile spore suspension medium (20% glycerol, 10% lactose), the spores were suspended and aliquots were frozen at −70° C. Working spore stocks were stored on CM slants in screw cap tubes at 4° C. The recombination event was through random integration of the plasmid into the *A. awamori* genome.

EXAMPLE 3

Culturing *A. awamori*

For enzyme production, spores were inoculated into 50 mL CM basal fermentation medium (5.0 μl Enzymatic Casein Hydrolysate; 5.0 g·L$^{-1}$ NH$_4$CL; 10.0 g·L$^{-1}$ Yeast Extract; 10.0 g·L$^{-1}$ Tryptone; 2.0 g·L$^{-1}$ MgSO$_4$.7H$_2$O; 50.0 μL$^{-1}$Soluble Starch; 50 mM Bis-Tris-Propane pH 7.0), and grown at 32° C., 225 rpm in 250 mL baffled flasks. The cultures were transferred to 1.0 L of basal fermentation medium in 2800 mL Fernbach flasks and grown under similar conditions. The flasks were harvested by filtration through Miracloth after 7-10 days of growth.

EXAMPLE 4

Purifying rCel7A from *A. awamori* Culture Broth

The purification of rCBH 1 from *A. awamori* fungal broths was started by filtration through glass fiber filters followed by concentration of the broth by using a 500 mL Amicon stirred cell concentrator with PM-10 cutoff filters. After the broth was concentrated to a volume of approximately 50 mL and was then extensively diafiltered by successive dilution and concentration with the stirred cell with 50 mM Bis-Tris pH 5.8 buffer to a point at which the conductivity of the solution was less than 2 mS/cm. The sample was then applied to a HiPrep 16/10 DEAE FF column (Amersham Biosciences) equilibrated with 50 mM Bis-Tris, pH 5.8 buffer with a flow rate 10 mL/min at 4° C. After the sample was loaded and the column washed extensively with equilibration buffer the bound fraction was eluted with a linear gradient of 0 to 1.0 M NaCl in the same equilibration buffer. The fractions containing activity on p-nitrophenol β-D-lactopyranoside were pooled and concentrated to a final volume of 10 mL using Amicon stirred cell concentrators and PM-10 cutoff filters (10,000 kDa nominal molecular weight cutoff). The enzyme was further purified and the buffer exchanged by means of size exclusion chromatography using a HiLoad 26/60 Superdex 200 column (Amersham Biosciences) in 20 mM acetate, 100 mM NaCl, pH 5.0 buffer. At this point the protein eluted as a single, symmetrical peak and the purity was confirmed as a single band when analyzed with a NuPage 4-12% Bis-Tris gradient gel using MOPS-SDS buffer (Invitrogen) according to the manufactures recommended conditions. Concentrations of purified proteins were determined by absorbance at 280 nm using the extinction coefficient and molecular weight calculated for Cel7A by the ProtParam Software obtained from the ExPASy website.

EXAMPLE 5

Production and Purification of Native *Penicillium funiculosum* Cel7A

Native Cel7A protein was produced from *Penicillium funiculosum* grown in two 500 mL cultures in CM-PSC broth (5 g·L$^{-1}$ Yeast Extract; 10 g·L$^{-1}$ phosphoric acid swollen cellulose; 5 g·L$^{-1}$ Tryptone; 20X Clutterbuck's Salts (120.0 g·L$^{-1}$ Na$_2$NO$_3$; 10.4 g·L$^{-1}$ KCl; 10.4 g·L$^{-1}$ MgSO$_4$.7H$_2$O; 30.4 g·L$^{-1}$ KH$_2$PO$_4$) 50 mL·L$^{-1}$) at pH 7.5 in baffled 1 L Erlenmeyer flasks. The flasks were inoculated with 1 mL of a spore suspension of *P. funiculosum* ATCC 62998 and incubated at 28° C. in a New Brunswick Scientific Model Innova 4230 shaking incubator at 225 rpm. The cultures were harvested by filtration following 7 days of growth.

The purification of the native Cel7 from *P. funiculosum* broth was started by filtration through glass fiber filters followed by concentration of the broth by using a 500 mL Amicon stirred cell concentrator with PM-10 cutoff membranes. The broth was first concentrated to a volume of approximately 50 mL followed by extensive diafiltration by successively diluting and concentrating the broth with 50 mM Bis-Tris.pH 5.8 buffer to a point at which the conductivity of the solution was less than 2 mS/cm. The sample was then applied to a 6 mL Resource Q column (Amersham Biosciences) equilibrated with 50 mM Bis-Tris, pH 5.8 buffer with a flow rate of 6 mL/min. After the sample was loaded and the column washed extensively with equilibration buffer and the bound fraction was eluted with a linear gradient of 0 to 1.0 M NaCl in the same equilibration buffer. The fractions containing activity on p-nitrophenol β-D lactopyranoside were pooled and concentrated to a final volume of 10 mL using Amicon stirred cell concentrators and PM-10 cutoff filters (10,000 kDa nominal molecular weight cutoff). The enzyme was further purified and the buffer exchanged by means of size exclusion chromatography using a HiLoad 26/60 Superdex 200 column (Amersham Biosciences) in 20 mM acetate, 100 mM NaCl, pH 5.0 buffer. The purity was confirmed as a single band using a NuPage 4-12% Bis-Tris gradient gel and MOPS-SDS buffer (Invitrogen) according to the manufacturer's recommended conditions. The concentration of the purified native Cel7 solution was determined by absorbance at 280 nm using the extinction coefficient and molecular weight calculated for Cel7A by the ProtParam tool on the ExPASy website.

EXAMPLE 6

Comparative Testing of Specific Performance

The purified rCel7A and Cel7A from Examples 4 and 5 were tested against other Cel7A enzymes. Test procedures included those described in "Hydrolysis of Cellulose Using Ternary Mixtures of Purified Cellulases," J. O. Baker, C. I. Ehrman, W. S. Adney, S. R. Thomas, and M. E. Himmel, *Appl. Biochem. Biotechnol.*, 70/72,395-403, (1998), and "A Membrane-Reactor Saccharification Assay to Evaluate the Performance of Cellulases Under Simulated SSF Conditions," J. O. Baker, T. B. Vinzant, C. I. Ehrman, W. S. Adney, and M. E. Himmel, *Appl. Biochem. Biotechnol*, 63-65, 585-595, (1997).

Diafiltration saccharification assays (DSA) were performed as disclosed in the above article by Baker et al. (1997) with the modifications that the membrane installed in the cells was a BioMax-5 (5,000 Da nom. MWCO, Millipore Corp.) rather than a PM-10 (10,000 Da nom. MWCO, Amicon, Inc.), and the buffer flow rate through the membrane was 0.020 ml/min. All assays were at pH 5.0 in acetate buffer with 0.02%(w/v) sodium azide-added. Assays were run at 38° C. as a compromise between the higher activities of the cellulases at still higher temperatures and the temperature-tolerance of *S. cerevisiae* D5A, the organism used in companion simultaneous saccharification and fermentation (SSF) assays.

Pretreated corn stover (1% wt/wt sulfuric acid for 2-4 min at 190° C.) was prepared for use as a DSA substrate. Substrate loadings averaged 96.4 mg (dry wt.) biomass (standard deviation, n=5, of 0.8% or less) per DSA cell loading, for cellulose loadings of 55.5 mg glucose per assay. Substrate loadings thus amounted to 4.3% (w/v, solids) or 2.5% (w/v, cellulose). Because the effective saccharification of crystalline cellulose requires the synergistic action of both endoglucanases and exoglucanases, the activities of Cel7A and rCel7A proteins were assayed in combination with the catalytic domain of *A. cellulolyticus* endoglucanase I (EIcd), used here as a standard endoglucanase. In all DSA protocols, the particular Cel7A species being tested was loaded at 27.8 mg per g cellulose, and the endoglucanase (EIcd) was loaded at 1.11 mg per g cellulose, resulting in a 95:5 molar ratio of exoglucanase to endoglucanase. Quantitation of product sugars in effluent fractions was by HPLC using an Aminex HPX-87H column operated at 65° C. with 0.01 N H$_2$SO$_4$ (0.6 mL/min) as mobile phase, in an Agilent Model 1100 chromatograph.

Protein Stability Measurements

The overall protein stability of rCel7A from Example 4 was measured by differential scanning microcalorimetry using a Microcal model VP-DSC calorimeter (Microcal, Inc., Northampton, Mass.), with data analysis by means of Origin for DSC software (Microcal). Thermograms were collected for samples containing 50 μg/mL protein at pH 5.0 in 20 mM sodium acetate with 100 mM NaCl. Calorimeter scan rate was 60° C./h.

Figure 5:
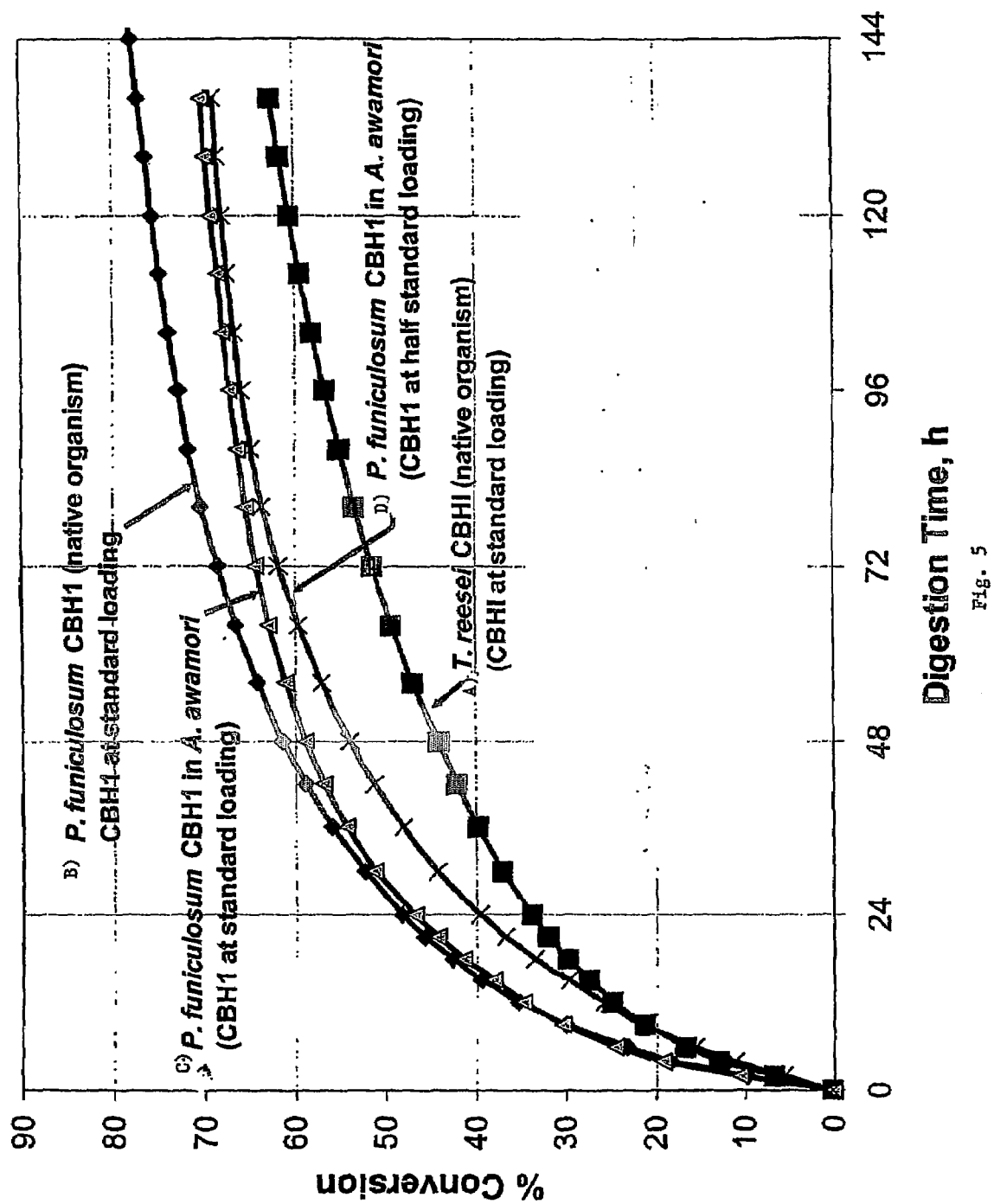
FIG. 5 shows a comparison of the specific performance of various Cel7A enzyme formulations (i.e., Cel7A or rCel7A and EIcd endoglucanase) on pretreated corn stover using the DSA assay, where the comparison includes that for standard loadings of purified recombinant Cel7A from *P. funiculosum* expressed in *A. awamori*; purified native Cel7A from *P. funiculosum*; and purified native Cel7A from *T. reesei*. Also illustrated in FIG. 5 is the one-half loading of purified recombinant Cel7A from *P. funiculosum* expressed in *A. awamori*.

FIG. 5 shows comparison saccharification results as a plot of percent conversion of pretreated corn stover over time. Saccharification conditions included a pH of 5.0, a temperature of 38° C., and a standard enzyme loading of Cel7A at 27.8 mg/g cellulose plus E1 endoglucanase at 1.13 mg/g cellulose. The comparison was between the specific performance of (A) native Cel7A from T reesei, (B) native Cel7A from *P. funiculosum*, (C) rCel7A from *P. funiculosum* expressed in *A. awamori*, and (D) a one-half loading of rCel7A from *P. funiculosum* expressed in *A. awamori*.

The results shown in FIG. 5 demonstrate advantages that are heretofore unknown in the art. Native *T. reesei* Cel7A is the current industry standard Cel7A enzyme used in cellulase formulations for biomass conversion. Surprisingly, an equivalent loading (27.8 mg protein/g cellulose) of purified Cel7A from *P. funiculosum* converted the pretreated corn stover substrate much more readily, with an approximate 69% conversion of cellulose being obtained at 72 hours, versus 52% conversion for the native *T. reesei* Cel7A. Furthermore, an equivalent loading of rCel7A from *P. funiculosum* expressed in *A. awamori* also yielded unexpectedly high performance, with 65% conversion of cellulose in 72 hours. This is important for process scale production of Cel7A, because heterologous expression of the *P. funiculosum* Cel7A from filamentous hosts is a viable large-scale production strategy. FIG. 5 also shows that at one-half loading (i.e., 13.9 mg protein/g cellulose) of the rCel7A *P. funiculosum* enzyme expressed in *A. awamori*, the performance on pretreated corn stover is still much greater than that of the native *T. reesei* Cel7A enzyme. These results show that the new *P. funiculosum* Cel7A +*A. cellulolyticus* EIcd endoglucanase formulation deliver greater than 2-fold increase in specific performance relative to the *T. reesei* enzyme. Importantly, the native and recombinant Cel7A from *P. funiculosum* display this specific performance under conditions suitable for commercial SSF processes (pH 5 and 38° C.).

In conclusion, the data presented in FIG. 5 confirm that the cellulose digestion kinetics are such that native *P. funiculosum* Cel7A and *P. funiculosum* rCel7A expressed in *A. awamori* outperform native *T. reesei* Cel7A by a factor of at least two, as demonstrated by the superior performance of *P. funiculosum* rCel7A (13.9 mg protein/g cellulose) relative to *T. reesei* Cel7A (27.8 mg/g cellulose) at all points measured over the interval from 0 to 136 hours.

EXAMPLE 7

Characterization of *P. funiculosum* rCel7A

The purified rCel7A from Example 6 was tested against other Cel7A enzymes that were not expressed in *A. awamori* to determine the maximal thermal transition temperature. Test procedures included the use of differential scanning calorimetry (DSC) instrumentation.

Figure 6:
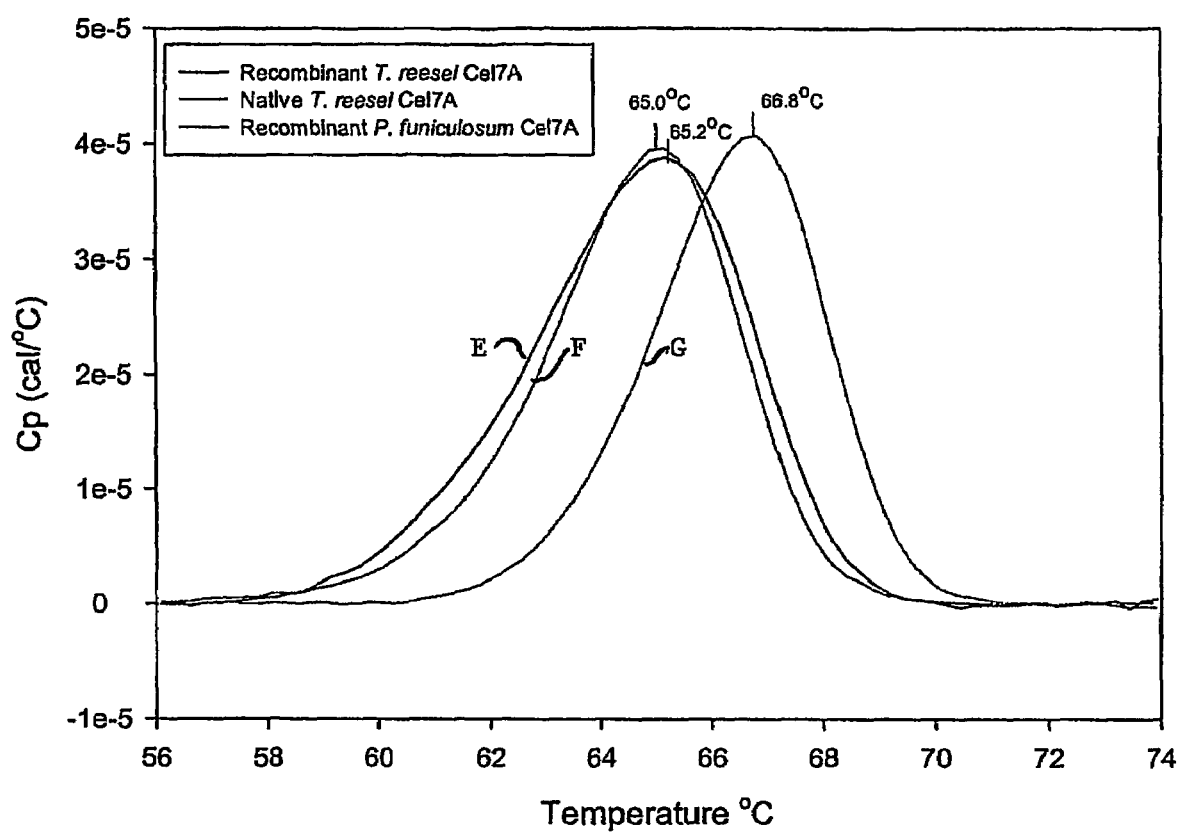
FIG. 6 provides a comparison of thermal transition temperatures between various purified Cel7A enzymes using DSC.

FIG. 6 shows the comparative DSC results. The rCel7A from *P. funiculosum* expressed in *A. awamori* shows an optimal activation temperature of 66.8° C., as compared to 65.0° C. and 68.2° C., respectively, for native *T. reesei* Cel7A and rCel7A from *T. reesei* expressed in *A. awamori*.

The foregoing discussion is intended to illustrate concepts by way of example with emphasis upon the preferred embodiments and instrumentalities. Accordingly, the disclosed embodiments and instrumentalities are not exhaustive of all options or mannerisms for practicing the disclosed principles hereof. The inventors hereby state their intention to rely upon the Doctrine of Equivalents in protecting the full scope and spirit of the invention.

The invention claimed is:

1. A cellulase formulation comprising:
an isolated and purified cellobiohydrolase 1 (glycosyl hydrolase family 7 (Cel 7)) enzyme having the polypeptide sequence of SEQ ID NO. 8; and an endoglucanase present in amount ranging from one percent (1%) to twenty percent (20%) of the molar concentration of the Cel 7 enzyme.

2. The cellulase formulation of claim 1, wherein the Cel7 enzyme is a heterologously expressed enzyme from a transgenic filamentous fungus.

3. The cellulase formulation of claim 2, wherein the transgenic filamentous fungus includes *Aspergillus*.

4. The cellulase formulation of claim 3, wherein the *Aspergillus* includes *Aspergillus awamori*.

5. The cellulase formulation of claim 2, wherein the transgenic filamentous fungus includes *Trichoderma*.

6. The cellulase formulation of claim 5, wherein the transgenic filamentous fungus includes *Trichoderma reesei*.

7. The cellulase formulation of claim 2, wherein the transgenic filamentous fungus includes *Penicillium* and a transgene coding for expression of the Cel7 enzyme is under control of a non-native promoter.

8. The cellulase formulation of claim 7, wherein the *Penicillium* comprises *Penicillium funiculosum*.

9. The cellulase formulation of claim 1, wherein the cellobiohydrolase formulation exhibits specific performance in saccharification of cellulase that exceeds by at least two-fold the specific performance of a comparable cellobiohydrolase formulation where Cel7A cellulase from *Trichoderma reesei* is substituted for the Cel7 enzyme.

10. The cellulase formulation of claim 9, wherein the specific performance is measured on corn stover.

11. The cellulase formulation of claim 1, wherein the endoglucanase comprises EIcd endoglucanase.

12. The cellulase formulation of claim 11, wherein the mixture comprises a 95:5 molar ratio of the Cel7A enzyme to EIcd endoglucanase.

13. The cellulase formulation of claim 1, further comprising at least one additional hydrolyzing enzyme.

14. The cellulase formulation of claim 1, wherein the Cel7 enzyme is characterized by a peak activation temperature of 68° C.

* * * * *

SEQUENCE LISTING

```
<160> NUMBER OF SEQ ID NOS: 10

<210> SEQ ID NO 1
<211> LENGTH: 24
<212> TYPE: DNA
<213> ORGANISM: Penicillium funiculosum

<400> SEQUENCE: 1
gtatacacgc tggatccgaa ctcc                                              24

<210> SEQ ID NO 2
<211> LENGTH: 34
<212> TYPE: DNA
<213> ORGANISM: Penicillium funiculosum

<400> SEQUENCE: 2
gttcaaggca gacattgctg aggtgtaatg atgc                                   34

<210> SEQ ID NO 3
<211> LENGTH: 34
<212> TYPE: DNA
<213> ORGANISM: Penicillium funiculosum

<400> SEQUENCE: 3
gcatcattac acctcagcaa tgtctgcctt gaac                                   34

<210> SEQ ID NO 4
<211> LENGTH: 41
<212> TYPE: DNA
<213> ORGANISM: Penicillium funiculosum
```

-continued

```
<400> SEQUENCE: 4
ataagaatgc ggccgcctac aaacattgag agtagtaagg g                          41

<210> SEQ ID NO 5
<211> LENGTH: 21
<212> TYPE: DNA
<213> ORGANISM: Penicillium funiculosum

<400> SEQUENCE: 5
acttcgttac cggctctaac g                                                21

<210> SEQ ID NO 6
<211> LENGTH: 21
<212> TYPE: DNA
<213> ORGANISM: Penicillium funiculosum

<400> SEQUENCE: 6
gaagtcacat ccgtcagggt c                                                21

<210> SEQ ID NO 7
<211> LENGTH: 1515
<212> TYPE: DNA
<213> ORGANISM: Penicillium funiculosum
<220> FEATURE:
<221> NAME/KEY: CDS
<222> LOCATION: (1)..(1515)
<223> OTHER INFORMATION:

<400> SEQUENCE: 7
```

| | | | | | | | | | | | | | | | | |
|---|---|---|---|---|---|---|---|---|---|---|---|---|---|---|---|---|
| cag | caa | att | ggt | act | tat | acc | gct | gaa | acc | cat | ccc | tct | ctg | agc | tgg | 48 |
| Gln | Gln | Ile | Gly | Thr | Tyr | Thr | Ala | Glu | Thr | His | Pro | Ser | Leu | Ser | Trp | |
| 1 | | | | 5 | | | | | 10 | | | | | 15 | | |
| tct | act | tgc | aaa | tcg | ggt | ggt | agc | tgc | acc | aca | aac | tcc | ggt | gcc | att | 96 |
| Ser | Thr | Cys | Lys | Ser | Gly | Gly | Ser | Cys | Thr | Thr | Asn | Ser | Gly | Ala | Ile | |
| | | | 20 | | | | | 25 | | | | | 30 | | | |
| acg | tta | gat | gcc | aac | tgg | cgt | tgg | gtc | cat | ggt | gtc | aat | acc | agc | acc | 144 |
| Thr | Leu | Asp | Ala | Asn | Trp | Arg | Trp | Val | His | Gly | Val | Asn | Thr | Ser | Thr | |
| | | | 35 | | | | | 40 | | | | | 45 | | | |
| aac | tgc | tac | act | ggc | aac | act | tgg | aat | agc | gcc | atc | tgc | gac | act | gat | 192 |
| Asn | Cys | Tyr | Thr | Gly | Asn | Thr | Trp | Asn | Ser | Ala | Ile | Cys | Asp | Thr | Asp | |
| | 50 | | | | | 55 | | | | | 60 | | | | | |
| gca | tcc | tgt | gcc | cag | gac | tgt | gct | ctc | gat | ggt | gct | gac | tac | tct | ggc | 240 |
| Ala | Ser | Cys | Ala | Gln | Asp | Cys | Ala | Leu | Asp | Gly | Ala | Asp | Tyr | Ser | Gly | |
| 65 | | | | | 70 | | | | | 75 | | | | | 80 | |
| acg | tac | ggt | atc | act | acc | tcc | ggc | aac | tca | ttg | cgc | ctg | aac | ttc | gtt | 288 |
| Thr | Tyr | Gly | Ile | Thr | Thr | Ser | Gly | Asn | Ser | Leu | Arg | Leu | Asn | Phe | Val | |
| | | | | 85 | | | | | 90 | | | | | 95 | | |
| acc | ggt | tcc | aac | gtc | gga | tct | cgt | act | tac | ctg | atg | gcc | gat | aac | acc | 336 |
| Thr | Gly | Ser | Asn | Val | Gly | Ser | Arg | Thr | Tyr | Leu | Met | Ala | Asp | Asn | Thr | |
| | | | 100 | | | | | 105 | | | | | 110 | | | |
| cac | tac | caa | atc | ttc | gat | ctg | ttg | aac | cag | gag | ttc | acc | ttc | acc | gtc | 384 |
| His | Tyr | Gln | Ile | Phe | Asp | Leu | Leu | Asn | Gln | Glu | Phe | Thr | Phe | Thr | Val | |
| | | | | 115 | | | | | 120 | | | | | 125 | | |
| gat | gtc | tcc | cac | ctc | cct | tgc | ggt | ttg | aac | ggt | gcc | ctc | tac | ttc | gtg | 432 |
| Asp | Val | Ser | His | Leu | Pro | Cys | Gly | Leu | Asn | Gly | Ala | Leu | Tyr | Phe | Val | |
| | | | 130 | | | | | 135 | | | | | 140 | | | |
| acc | atg | gat | gcc | gac | ggt | ggc | gtc | tcc | aag | tac | ccc | aac | aac | aag | gcc | 480 |
| Thr | Met | Asp | Ala | Asp | Gly | Gly | Val | Ser | Lys | Tyr | Pro | Asn | Asn | Lys | Ala | |
| 145 | | | | | 150 | | | | | 155 | | | | | 160 | |
| ggt | gct | cag | tac | ggt | gtt | gga | tac | tgt | gac | tct | caa | tgc | cct | cgt | gac | 528 |
| Gly | Ala | Gln | Tyr | Gly | Val | Gly | Tyr | Cys | Asp | Ser | Gln | Cys | Pro | Arg | Asp | |
| | | | | 165 | | | | | 170 | | | | | 175 | | |

-continued

| | |
|---|---|
| ttg aag ttc atc gct ggt cag gcc aac gtt gag ggc tgg acg ccc tcc<br>Leu Lys Phe Ile Ala Gly Gln Ala Asn Val Glu Gly Trp Thr Pro Ser<br>        180                    185                190 | 576 |
| gcc aac aac gcc aac act gga att ggc aat cac gga gct tgc tgc gcg<br>Ala Asn Asn Ala Asn Thr Gly Ile Gly Asn His Gly Ala Cys Cys Ala<br>       195                     200                  205 | 624 |
| gag ctt gat atc tgg gag gca aac agc atc tca gag gcc ttg act cct<br>Glu Leu Asp Ile Trp Glu Ala Asn Ser Ile Ser Glu Ala Leu Thr Pro<br>210                    215                  220 | 672 |
| cac cct tgc gat aca ccc ggt cta tct gtt tgc act act gat gcc tgc<br>His Pro Cys Asp Thr Pro Gly Leu Ser Val Cys Thr Thr Asp Ala Cys<br>225                    230                235              240 | 720 |
| ggt ggc acc tac agc tct gat cgt tac gcc ggt acc tgc gac cct gat<br>Gly Gly Thr Tyr Ser Ser Asp Arg Tyr Ala Gly Thr Cys Asp Pro Asp<br>                     245                 250                 255 | 768 |
| gga tgt gac ttc aac cct tac cgc ctt ggt gtc act gac ttc tac ggc<br>Gly Cys Asp Phe Asn Pro Tyr Arg Leu Gly Val Thr Asp Phe Tyr Gly<br>            260                    265                 270 | 816 |
| tcc ggc aag acc gtt gac acc acc aag ccc ttt acc gtt gtg act caa<br>Ser Gly Lys Thr Val Asp Thr Thr Lys Pro Phe Thr Val Val Thr Gln<br>                275                    280                285 | 864 |
| ttc gtc act aac gac ggt acc tcc acc ggt tcc ctc tcc gag atc aga<br>Phe Val Thr Asn Asp Gly Thr Ser Thr Gly Ser Leu Ser Glu Ile Arg<br>290                    295                  300 | 912 |
| cgt tac tac gtt cag aac ggc gtt gtc atc ccc cag cct tcc tcc aag<br>Arg Tyr Tyr Val Gln Asn Gly Val Val Ile Pro Gln Pro Ser Ser Lys<br>305                    310                315              320 | 960 |
| atc tcc gga atc agc gga aat gtc atc aac tcc gac tac tgc gct gct<br>Ile Ser Gly Ile Ser Gly Asn Val Ile Asn Ser Asp Tyr Cys Ala Ala<br>                     325                 330                335 | 1008 |
| gaa att tcc acc ttt ggc ggg act gcc tcc ttc agc aaa cac ggt ggc<br>Glu Ile Ser Thr Phe Gly Gly Thr Ala Ser Phe Ser Lys His Gly Gly<br>            340                    345                 350 | 1056 |
| ttg aca aac atg gcc gct ggt atg gaa gct ggt atg gtc ttg gtc atg<br>Leu Thr Asn Met Ala Ala Gly Met Glu Ala Gly Met Val Leu Val Met<br>               355                    360                365 | 1104 |
| agt ttg tgg gac gac tac gcc gtc aac atg ctc tgg ctc gac agc acc<br>Ser Leu Trp Asp Asp Tyr Ala Val Asn Met Leu Trp Leu Asp Ser Thr<br>370                    375                  380 | 1152 |
| tac cct aca aac gcg act ggt acc ccc ggt gcc gct cgt ggt acc tgc<br>Tyr Pro Thr Asn Ala Thr Gly Thr Pro Gly Ala Ala Arg Gly Thr Cys<br>385                    390                395              400 | 1200 |
| gct acc act tct ggg gac ccc aag acc gtt gaa tca caa tcc ggc agc<br>Ala Thr Thr Ser Gly Asp Pro Lys Thr Val Glu Ser Gln Ser Gly Ser<br>                     405                 410                415 | 1248 |
| tcc tat gtc acc ttc tct gac att cgg gtt ggt cct ttc aat tct acg<br>Ser Tyr Val Thr Phe Ser Asp Ile Arg Val Gly Pro Phe Asn Ser Thr<br>                    420                  425              430 | 1296 |
| ttc agc ggt ggt tct agc acc ggt ggc agc act act act acc gcc agc<br>Phe Ser Gly Gly Ser Ser Thr Gly Gly Ser Thr Thr Thr Thr Ala Ser<br>               435                  440                445 | 1344 |
| cgc acc acc acc acc tcg gcc tct tcc acc tct act tcc agc acc tct<br>Arg Thr Thr Thr Thr Ser Ala Ser Ser Thr Ser Thr Ser Ser Thr Ser<br>450                    455                  460 | 1392 |
| act ggc act gga gtc gct ggt cac tgg ggt cag tgt ggt ggc cag ggc<br>Thr Gly Thr Gly Val Ala Gly His Trp Gly Gln Cys Gly Gly Gln Gly<br>465                    470                475              480 | 1440 |
| tgg act ggc cct acc acc tgt gtt agt gga acc aca tgc acc gtc gtg<br>Trp Thr Gly Pro Thr Thr Cys Val Ser Gly Thr Thr Cys Thr Val Val | 1488 |

```
                    485            490            495
aac cct tac tac tct caa tgt ttg tag                         1515
Asn Pro Tyr Tyr Ser Gln Cys Leu
                500
```

<210> SEQ ID NO 8
<211> LENGTH: 504
<212> TYPE: PRT
<213> ORGANISM: Penicillium funiculosum

<400> SEQUENCE: 8

```
Gln Gln Ile Gly Thr Tyr Thr Ala Glu Thr His Pro Ser Leu Ser Trp
1               5                   10                  15

Ser Thr Cys Lys Ser Gly Gly Ser Cys Thr Thr Asn Ser Gly Ala Ile
            20                  25                  30

Thr Leu Asp Ala Asn Trp Arg Trp Val His Gly Val Asn Thr Ser Thr
        35                  40                  45

Asn Cys Tyr Thr Gly Asn Thr Trp Asn Ser Ala Ile Cys Asp Thr Asp
    50                  55                  60

Ala Ser Cys Ala Gln Asp Cys Ala Leu Asp Gly Ala Asp Tyr Ser Gly
65                  70                  75                  80

Thr Tyr Gly Ile Thr Thr Ser Gly Asn Ser Leu Arg Leu Asn Phe Val
                85                  90                  95

Thr Gly Ser Asn Val Gly Ser Arg Thr Tyr Leu Met Ala Asp Asn Thr
            100                 105                 110

His Tyr Gln Ile Phe Asp Leu Leu Asn Gln Glu Phe Thr Phe Thr Val
        115                 120                 125

Asp Val Ser His Leu Pro Cys Gly Leu Asn Gly Ala Leu Tyr Phe Val
    130                 135                 140

Thr Met Asp Ala Asp Gly Gly Val Ser Lys Tyr Pro Asn Asn Lys Ala
145                 150                 155                 160

Gly Ala Gln Tyr Gly Val Gly Tyr Cys Asp Ser Gln Cys Pro Arg Asp
                165                 170                 175

Leu Lys Phe Ile Ala Gly Gln Ala Asn Val Glu Gly Trp Thr Pro Ser
            180                 185                 190

Ala Asn Asn Ala Asn Thr Gly Ile Gly Asn His Gly Ala Cys Cys Ala
        195                 200                 205

Glu Leu Asp Ile Trp Glu Ala Asn Ser Ile Ser Glu Ala Leu Thr Pro
    210                 215                 220

His Pro Cys Asp Thr Pro Gly Leu Ser Val Cys Thr Thr Asp Ala Cys
225                 230                 235                 240

Gly Gly Thr Tyr Ser Ser Asp Arg Tyr Ala Gly Thr Cys Asp Pro Asp
                245                 250                 255

Gly Cys Asp Phe Asn Pro Tyr Arg Leu Gly Val Thr Asp Phe Tyr Gly
            260                 265                 270

Ser Gly Lys Thr Val Asp Thr Lys Pro Phe Thr Val Val Thr Gln
        275                 280                 285

Phe Val Thr Asn Asp Gly Thr Ser Thr Gly Ser Leu Ser Glu Ile Arg
    290                 295                 300

Arg Tyr Tyr Val Gln Asn Gly Val Val Ile Pro Gln Pro Ser Ser Lys
305                 310                 315                 320

Ile Ser Gly Ile Ser Gly Asn Val Ile Asn Ser Asp Tyr Cys Ala Ala
                325                 330                 335

Glu Ile Ser Thr Phe Gly Gly Thr Ala Ser Phe Ser Lys His Gly Gly
            340                 345                 350
```

-continued

```
Leu Thr Asn Met Ala Ala Gly Met Glu Ala Gly Met Val Leu Val Met
        355                 360                 365
Ser Leu Trp Asp Asp Tyr Ala Val Asn Met Leu Trp Leu Asp Ser Thr
        370                 375                 380
Tyr Pro Thr Asn Ala Thr Gly Thr Pro Gly Ala Ala Arg Gly Thr Cys
385                 390                 395                 400
Ala Thr Thr Ser Gly Asp Pro Lys Thr Val Glu Ser Gln Ser Gly Ser
                405                 410                 415
Ser Tyr Val Thr Phe Ser Asp Ile Arg Val Gly Pro Phe Asn Ser Thr
                420                 425                 430
Phe Ser Gly Gly Ser Ser Thr Gly Gly Ser Thr Thr Thr Ala Ser
        435                 440                 445
Arg Thr Thr Thr Thr Ser Ala Ser Ser Thr Ser Thr Ser Ser Thr Ser
        450                 455                 460
Thr Gly Thr Gly Val Ala Gly His Trp Gly Gln Cys Gly Gly Gln Gly
465                 470                 475                 480
Trp Thr Gly Pro Thr Thr Cys Val Ser Gly Thr Thr Cys Thr Val Val
                485                 490                 495
Asn Pro Tyr Tyr Ser Gln Cys Leu
                500

<210> SEQ ID NO 9
<211> LENGTH: 75
<212> TYPE: DNA
<213> ORGANISM: Penicillium funiculosum

<400> SEQUENCE: 9
atgtctgcct tgaactcttt caatatgtac aagagcgccc tcatcttggg ctccttgctg    60
gcaacagctg gtgct                                                    75

<210> SEQ ID NO 10
<211> LENGTH: 504
<212> TYPE: PRT
<213> ORGANISM: Penicillium funiculosum

<400> SEQUENCE: 10

Gln Gln Ile Gly Thr Tyr Thr Ala Glu Thr His Pro Ser Leu Ser Trp
1               5                   10                  15
Ser Thr Cys Lys Ser Gly Gly Ser Cys Thr Thr Asn Ser Gly Ala Ile
            20                  25                  30
Thr Leu Asp Ala Asn Trp Arg Trp Val His Gly Val Asn Thr Ser Thr
        35                  40                  45
Asn Cys Tyr Thr Gly Asn Thr Trp Asn Ser Ala Ile Cys Asp Thr Asp
    50                  55                  60
Ala Ser Cys Ala Gln Asp Cys Ala Leu Asp Gly Ala Asp Tyr Ser Gly
65                  70                  75                  80
Thr Tyr Gly Ile Thr Thr Ser Gly Asn Ser Leu Arg Leu Asn Phe Val
                85                  90                  95
Thr Gly Ser Asn Val Gly Ser Arg Thr Tyr Leu Met Ala Asp Asn Thr
            100                 105                 110
His Tyr Gln Ile Phe Asp Leu Leu Asn Gln Glu Phe Thr Phe Thr Val
        115                 120                 125
Asp Val Ser His Leu Pro Cys Gly Leu Asn Gly Ala Leu Tyr Phe Val
    130                 135                 140
Thr Met Asp Ala Asp Gly Gly Val Ser Lys Tyr Pro Asn Asn Lys Ala
```

-continued

```
145                 150                 155                 160
Gly Ala Gln Tyr Gly Val Gly Tyr Cys Asp Ser Gln Cys Pro Arg Asp
                165                 170                 175
Leu Lys Phe Ile Ala Gly Gln Ala Asn Val Glu Gly Trp Thr Pro Ser
                180                 185                 190
Ala Asn Asn Ala Asn Thr Gly Ile Gly Asn His Gly Ala Cys Cys Ala
                195                 200                 205
Glu Leu Asp Ile Trp Glu Ala Asn Ser Ile Ser Glu Ala Leu Thr Pro
                210                 215                 220
His Pro Cys Asp Thr Pro Gly Leu Ser Val Cys Thr Thr Asp Ala Cys
225                 230                 235                 240
Gly Gly Thr Tyr Ser Ser Asp Arg Tyr Ala Gly Thr Cys Asp Pro Asp
                245                 250                 255
Gly Cys Asp Phe Asn Pro Tyr Arg Leu Gly Val Thr Asp Phe Tyr Gly
                260                 265                 270
Ser Gly Lys Thr Val Asp Thr Thr Lys Pro Phe Thr Val Val Thr Gln
                275                 280                 285
Phe Val Thr Asn Asp Gly Thr Ser Thr Gly Ser Leu Ser Glu Ile Arg
                290                 295                 300
Arg Tyr Tyr Val Gln Asn Gly Val Val Ile Pro Gln Pro Ser Ser Lys
305                 310                 315                 320
Ile Ser Gly Ile Ser Gly Asn Val Ile Asn Ser Asp Tyr Cys Ala Ala
                325                 330                 335
Glu Ile Ser Thr Phe Gly Gly Thr Ala Ser Phe Ser Lys His Gly Gly
                340                 345                 350
Leu Thr Asn Met Ala Ala Gly Met Glu Ala Gly Met Val Leu Val Met
                355                 360                 365
Ser Leu Trp Asp Asp Tyr Ala Val Asn Met Leu Trp Leu Asp Ser Thr
                370                 375                 380
Tyr Pro Thr Asn Ala Thr Gly Thr Pro Gly Ala Ala Arg Gly Thr Cys
385                 390                 395                 400
Ala Thr Thr Ser Gly Asp Pro Lys Thr Val Glu Ser Gln Ser Gly Ser
                405                 410                 415
Ser Tyr Val Thr Phe Ser Asp Ile Arg Val Gly Pro Phe Asn Ser Thr
                420                 425                 430
Phe Ser Gly Gly Ser Ser Thr Gly Gly Ser Thr Thr Thr Thr Ala Ser
                435                 440                 445
Arg Thr Thr Thr Ser Ala Ser Ser Thr Ser Thr Ser Ser Thr Ser
                450                 455                 460
Thr Gly Thr Gly Val Ala Gly His Trp Gly Gln Cys Gly Gly Gln Gly
465                 470                 475                 480
Trp Thr Gly Pro Thr Thr Cys Val Ser Gly Thr Thr Cys Thr Val Val
                485                 490                 495
Asn Pro Tyr Tyr Ser Gln Cys Leu
                500
```